United States Patent [19]

Wittenberger et al.

[11] Patent Number: 5,284,954
[45] Date of Patent: Feb. 8, 1994

[54] PROCESS FOR THE PREPARATION OF TETRAZOLES

[75] Inventors: Steven J. Wittenberger; Bikshandar A. Narayanan, both of Mundelein; Anthony R. Haight, Park City; David Scarpetti, Evanston, all of Ill.

[73] Assignee: Abbott Laboratories, Abbott Park, Ill.

[21] Appl. No.: 954,645

[22] Filed: Sep. 30, 1992

Related U.S. Application Data

[63] Continuation-in-part of Ser. No. 819,537, Jan. 10, 1992, Pat. No. 5,210,206, which is a continuation-in-part of Ser. No. 744,241, Aug. 15, 1991, abandoned, which is a continuation-in-part of Ser. No. 580,400, Sep. 10, 1990, abandoned.

[51] Int. Cl.$^5$ .................. C07D 401/10; C07D 257/04
[52] U.S. Cl. ..................... 546/276; 548/252; 548/253; 548/254
[58] Field of Search ............... 546/276; 548/252, 253, 548/254

[56] References Cited

FOREIGN PATENT DOCUMENTS 291969 11/1988 European Pat. Off. .
475206 3/1992 European Pat. Off. .
487745 6/1992 European Pat. Off. .
499415 8/1992 European Pat. Off. .
59-98023 6/1984 Japan .

OTHER PUBLICATIONS

H. Wolff, Organic Reactions, vol. 111 pp. 307-336 (1965).
J. Mihina, et al., J. Org. Chem. 15 (1950).
E. Ettenhuber, et al., Chem. Ber 101 743 (1968).

Primary Examiner—Nicholas S. Rizzo
Assistant Examiner—Y. N. Gupta
Attorney, Agent, or Firm—Steven R. Crowley

[57] ABSTRACT

The present invention relates to a process for the preparation of 5-aryl tetrazoles of the formula:

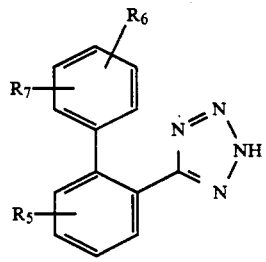

or a salt thereof comprising reacting an aryl nitrile with a trisubstituted silyl azide and a disubstituted tin oxide.

13 Claims, No Drawings

PROCESS FOR THE PREPARATION OF TETRAZOLES

This is a continuation-in-part of U.S. patent application Ser. No. 819,537, filed Jan. 10, 1992 now U.S. Pat. No. 5,210,206, which is a continuation-in-part of U.S. patent application Ser. No. 744,241, filed Aug. 15, 1991 now abandoned, which is a continuation-in-part of U.S. patent application Ser. No. 580,400, filed Sep. 10, 1990, now abandoned.

TECHNICAL FIELD

The present invention relates to a process for the preparation of tetrazoles. In particular, this invention is directed to a process for the preparation of 5-aryl tetrazoles.

BACKGROUND OF THE INVENTION

Typically, tetrazoles are prepared from the reaction of an hydrazoic acid source (e.g. sodium azide and ammonium chloride) and an acceptor group such as a cyanate or a nitrile (Organic Reactions, 3, 307 (1946)). For example, heating an aryl or alkyl nitrile with hydrazoic acid, generated from sodium azide and hydrochloric acid, in an inert solvent in a sealed tube for 96–120 hours at temperatures from 120°–150° C. affords the 5-aryl or 5-alkyltetrazole (Mihina, J. S., Herbst, R. M. J. Org. Chem. 15, 1082 (1950)). Alternatively, 5-aryl tetrazoles can be prepared by brominating the appropriately substituted tolyl compound, converting the resulting dibromo-compound to the diazido-compound with sodium azide and then cyclizing by heating in refluxing dimethylformamide to give the tetrazole (Jpn. Kokai Tokkyo Koho JP 59 98,023).

Hydrazoic acid itself is extremely poisonous, explosive, cannot readily be used in stainless steel reactors and has a low boiling point (37° C.). An alternative source of azide anion is trialkyltin azide (European Patent Application Number 291969). Trialkyltin azide is prepared from a trialkyltin chloride, which is volatile and toxic, and sodium azide. This reagent must be used in stoichiometric amount. Trimethylsilyl azide has also been cited as an azide source reported to react with benzonitrile (Ettenhuber, E., Rühlmann, K. Chem. Ber. 101, 743 (1968)).

Most of the above-mentioned processes involve the use of hydrazoic acid or an azide source which forms hydrazoic acid in situ and, generally, elevated temperatures are required for reaction. These reaction conditions can be hazardous. Therefore, there is a continuing need for improved processes for the preparation of tetrazoles.

DISCLOSURE OF THE INVENTION

The present invention relates to a process for the preparation of 5-substituted tetrazoles or a salt thereof. This process involves the reaction of a nitrile with a substituted silyl azide in the presence of a substituted tin oxide.

In particular, the present invention relates to a process for the preparation of 5-aryl tetrazoles or a salt thereof. The process of this invention is shown in Scheme I. Aryl nitrile 1 is reacted with from about 1.0 to about 8.0 molar equivalents of substituted silyl azide 2 ($R_2$ at each occurrence is independently selected from loweralkyl and phenyl) and from about 0.05 to about 1.0 molar equivalents of substituted tin oxide 3 ($R_3$ is independently selected at each occurrance from loweralkyl and phenyl or $(R_3)_2$ represents $-(CH_2)_n-$ wherein n is 4, 5 or 6) in an inert solvent (for example, toluene or decalin or dimethylformamide or xylene and the like) at a temperature of from about 65° C. to about 140° C. to give tetrazole 4. In aryl nitrile 1, $R_1$ is selected from phenyl, naphthyl,

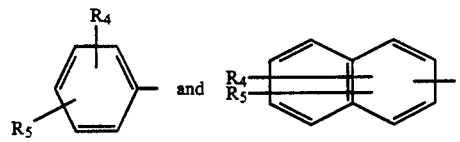

wherein $R_4$ is (1) loweralkyl, (2) halo, (3) alkoxy, (4) amino, (5) alkylamino, (6) dialkylamino, (7) alkoxycarbonyl, (8) alkoxycarbonylalkyl or

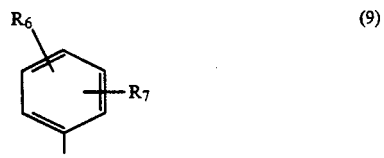

(9)

wherein $R_6$ is (i) loweralkyl, (ii) $-CHO$, (iii) $-CO_2R_8$ wherein $R_8$ is loweralkyl or a carboxy protecting group or (iv) loweralkyl substituted with $-N(R_9)(R_{10})$ wherein $R_9$ is hydrogen, loweralkyl, alkoxyalkyl, alkenyl, alkynyl, cycloalkyl or cycloalkylalkyl and $R_{10}$ is hydrogen, an nitrogen-protecting group or

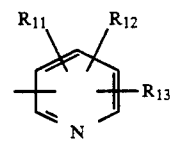

wherein $R_{11}$ is $-CO_2R_{14}$ wherein $R_{14}$ is loweralkyl or a carboxy protecting group and $R_{12}$ and $R_{13}$ are independently selected from hydrogen, loweralkyl and halo and $R_7$ is hydrogen, loweralkyl, alkoxy, alkoxyalkyl or halo and $R_5$ is (1) hydrogen, (2) loweralkyl, (3) alkoxy or (4) halo.

In a preferred embodiment of the invention, nitrile 1 is reacted with about 2 molar equivalents of substituted silylazide 2 ($R_2$ is methyl) and from about 0.1 to about 1.0 molar equivalent of substituted tin oxide 3 ($R_3$ is butyl, methyl or phenyl) in toluene at a temperature of from about 65° C. to about 110° C. to give tetrazole 4. In a more preferred embodiment of the invention, $R_2$ is methyl and $R_3$ is butyl, methyl or phenyl.

In the process of the present invention, excess azide can be removed from the reaction mixture prior to isolating the product by adding acetonitrile to the crude reaction mixture and heating. The resulting 5-methyltetrazole that is formed is water soluble and can be removed from the reaction mixture by extraction with water.

In the process of the present invention, preferred arylnitriles 1 are compounds of the formula:

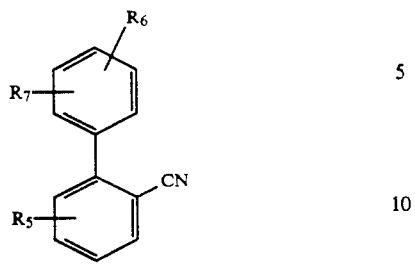

wherein $R_5$ is hydrogen, loweralkyl, alkoxy or halo, $R_7$ is hydrogen, loweralkyl, alkoxy, alkoxyalkyl or halo and $R_6$ is loweralkyl or —$CH_2N(R_9)(R_{10})$ wherein $R_9$ is hydrogen, loweralkyl, alkoxyalkyl, alkenyl, alkynyl, cycloalkyl or cycloalkylalkyl and $R_{10}$ is hydrogen or an nitrogen-protecting group. Particularly preferred are those compounds wherein $R_6$ is in the 4'-position of the biphenyl nitrile.

In the process of the present invention, preferred arylnitriles 1 are also compounds of the formula:

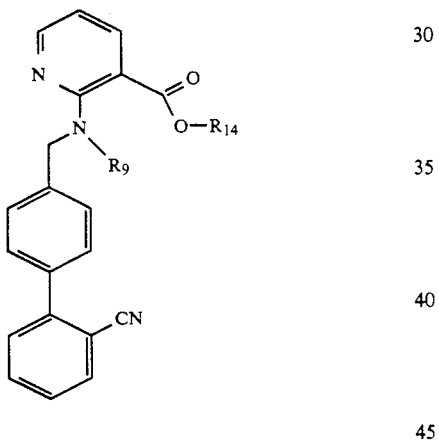

wherein $R_9$ is hydrogen, loweralkyl, alkoxyalkyl, alkenyl, alkynyl, cycloalkyl or cycloalkylalkyl and $R_{14}$ is hydrogen, loweralkyl or a carboxy protecting group.

A more preferred embodiment of this invention is shown in Scheme II. Biphenyl nitrile 5 ($R_9$ is loweralkyl) is reacted with a substituted silylazide and a substituted tin oxide to give tetrazole 6. In an even more preferred embodiment, biphenyl nitrile 5 ($R_9$ is n-propyl) is reacted with trimethylsilylazide and dibutyltin oxide in toluene to give tetrazole 6.

Another more preferred embodiment of this invention is shown in Scheme III. Compound 7 ($R_9$ is loweralkyl and $R_{14}$ is loweralkyl) is reacted with a substituted silylazide and a substituted tin oxide to give tetrazole 8. In an even more preferred embodiment, compound 7 ($R_9$ is n-propyl and $R_{14}$ is methyl) is reacted with trimethylsilylazide and dibutyltin oxide in toluene to give tetrazole 8.

SCHEME I

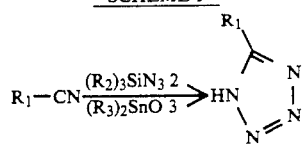

SCHEME II

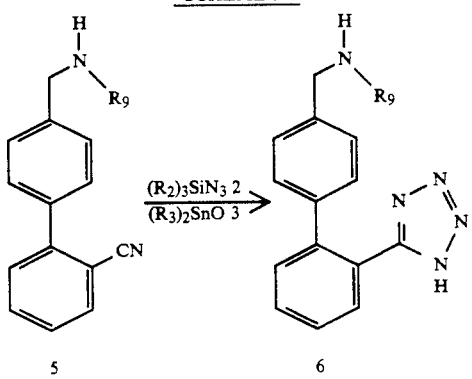

SCHEME III

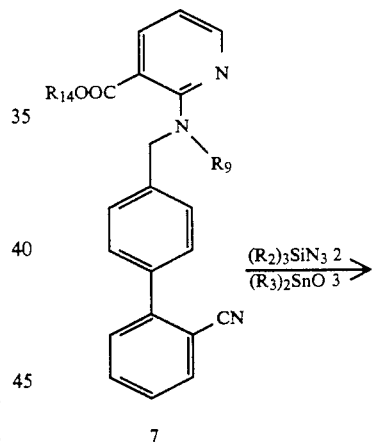

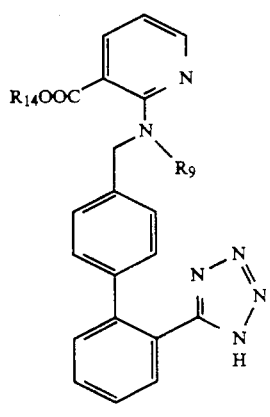

Compounds of the formula 4, 6 and 8 are useful as intermediates in the preparation of angiotensin II antagonists. See European Patent Application No. EP475206, published Mar. 18, 1992.

The term "loweralkyl" as used herein refers to a straight or branched chain alkyl radical having from 1 to 7 carbon atoms including, but not limited to, methyl, ethyl, n-propyl, iso-propyl, n-butyl, iso-butyl, sec-butyl, n-pentyl, 2-methylbutyl, 2,2-dimethylpropyl, n-hexyl, 2-methylpentyl, 2,2-dimethylbutyl, n-heptyl and the like.

The term "alkenyl" or "lower alkenyl" as used herein refers to a branched or straight chain of two to ten carbon atoms and which also has one or more carbon-carbon double bonds.

The term "alkynyl" or "lower alkynyl" as used herein refers to a branched or straight chain of two to ten carbon atoms and which also has one or more carbon-carbon triple bonds.

The term "alkoxyalkyl" as used herein refers to a loweralkyl radical to which is appended a loweralkoxy group.

The term "aryl" as used herein refers to a $C_6$ monocyclic aromatic ring system or a $C_9$ or $C_{10}$ bicyclic carbocyclic ring system having one or two aromatic rings including, but not limited to, phenyl, naphthyl, indanyl, indenyl, tetrahydronaphthyl and the like. Aryl groups can be unsubstituted or substituted with one, two or three substituents independently selected from loweralkyl, halo, loweralkoxy, loweralkoxycarbonyl, loweralkoxycarbonylalkyl, hydroxy, halo, mercapto, amino, loweralkylamino or dialkylamino.

The term "carboxy-protecting group" as used herein refers to a carboxy group which has been esterified with one of the commonly used carboxylic acid protecting ester groups employed to block or protect the carboxylic acid functionality while the reactions involving other functional sites of the compound are carried out. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975). Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of whcih are incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press:New York (1987). Representative protecting groups include $C_1$ to $C_8$ alkyl (e.g., methyl, ethyl or tertiary butyl and the like), benzyl and substituted derivatives thereof such as alkoxybenzyl or nitrobenzyl groups and the like, dialkylaminoalkyl (e.g., dimethylaminoethyl and the like), alkanoyloxyalkyl groups such as pivaloyloxymethyl or propionyloxymethyl and the like.

The term "cycloalkyl" as used herein refers to an alicyclic ring having 3 to 7 carbon atoms including, but not limited to, cyclopropyl, cyclopentyl, cyclohexyl and the like.

The term "cycloalkylalkyl" as used herein refers to a cycloalkyl residue appended to a loweralkyl radical and includes, but is not limited to, cyclohexylmethyl, cyclopentylmethyl and the like.

The term "halo" or "halogen" as used herein refers to Cl, Br, F or I.

The term "alkoxy" or "loweralkoxy" as used herein refers to $R_{20}O—$ wherein $R_{20}$ is a loweralkyl group.

The term "alkylamino" as used herein refers to $—NHR_{21}$ wherein $R_{21}$ is a loweralkyl group.

The term "dialkylamino" as used herein refers to $—NR_{22}R_{23}$ wherein $R_{22}$ and $R_{23}$ are independently selected from loweralkyl.

The term "alkoxycarbonyl" as used herein refers to $—C(O)R_{24}$ wherein $R_{24}$ is an alkoxy group.

The term "alkoxycarbonylalkyl" as used herein refers to a loweralkyl radical to which is appended an alkoxycarbonyl group.

The term "N-protecting group", "nitrogen-protecting group" or "N-protected" as used herein refers to those groups intended to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, benzyl wherein the phenyl ring is substituted with one, two or three alkoxy groups, triphenylmethyl (trityl), triphenylmethyl wherein one or more of the phenyl rings is substituted with a loweralkyl, halo or alkoxy group, t-butyloxycarbonyl (Boc), benzyloxycarbonyl (Cbz) and the like.

The term "salt" as used herein refers to both acid addition and alkali or alkaline earth metal salts. (S. M. Berge, et al. describe pharmaceutically acceptable salts in detail in J. Pharmaceutical Sciences, 66, 1, (1977)). The salts can be prepared in situ during the final isolation and purification of the compounds of formula (4), or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, maleate, methanesulfonate, 2-naphthalenesulfonate, nicotinate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, calcium, potassium, magnesium salts and the like.

The following examples will serve to further illustrate the process of the invention.

EXAMPLE 1

N-(4-Bromophenylmethyl)-N-propylamine

To 4-bromobenzaldehyde (100 g, 0.54 mol) and n-propylamine (36.3 g, 0.60 mol) in methanol (100 mL) was added 5% platinum on carbon (1.00 g). This mixture was shaken in a Parr hydrogenation reactor overnight to complete formation of the Schiff base. The reaction was then hydrogenated under 4 atmospheres of hydrogen until the theoretical uptake of hydrogen had been consumed. The catalyst was removed by filtration through a 0.45μ nylon frit and washed with methanol. The filtrate was concentrated under reduced pressure and the residue obtained dissolved in ether (500 mL). The ether solution was washed with water (2×100 mL), 10% sodium bicarbonate solution (2×100 mL), and water (2×100 mL), dried over magnesium sulfate, filtered, and concentrated under reduced pressure to afford the crude title compound (121.34 g). GC-MS showed this material to be 98.5% pure product containing 1.5% of the desbromo compound; the yield is 96.93% based on the GC purity of the product obtained. A sample of material thus obtained was purified by bulb-to-bulb distillation (bath temperature 130°–150° C., 0.18 torr). $^1$H NMR (CDCl$_3$, 300 MHz) δ0.92 (t, J=7.4 Hz, 3H), 1.36 (bs, 1H), 1.53 (tq, J$_1$=J$_2$=7.4 Hz, 2H), 2.57 (t, J=7.4 Hz, 2H), 3.74 (s, 2H), 7.20 (d, J=9 Hz, 2H), 7.44 (d, J=9 Hz, 2H). IR (film) 1430, 1060 cm$^{-1}$. MS (DCl/NH$_3$) m/e 228, 230 (M+H)$^+$. Anal calcd for C$_{10}$H$_{14}$BrN: C, 52.64; H, 6.18; N, 6.14. Found: C, 53.12; H, 6.24; N, 6.18.

EXAMPLE 2

N-(4-Bromophenylmethyl)-N-propylamine-N-tritylamine

To a stirred solution of the compound resulting from Example 1 (49.7 g, 0.218 mol) dissolved in methylene chloride (500 mL) under nitrogen at 0° C. was added triethylamine (36 mL), followed by tritylchloride (63.8 g, 0.229 mol). The reaction mixture was allowed to warm to ambient temperature and stirred for an additional 18 hours. The resultant slurry was diluted with methylene chloride (1 L) and washed with water (2×), 10% aqueous sodium bicarbonate, and brine. Drying over magnesium sulfate and concentrating under reduced pressure gave a pale yellow oil. Crystallization from ethanol (500 mL) afforded the title compound as a white solid (103 g, 83%). m.p. 136°–137° C. $^1$H NMR (CDCl$_3$, 300 MHz) δ0.47 (bt, J=7.5 Hz, 3H), 0.95 (m, 2H), 2.24 (m, 2H), 3.57 (s, 2H), 7.17 (bdd, J$_1$=J$_2$=7.5 Hz, 3H), 7.27 (dd, J=7.5 Hz, 6H), 7.45 (s, 4H), 7.60 (d, J=7.5 Hz, 2H). IR (KBr) 1482, 710 cm$^{-1}$. Anal calcd for C$_{29}$H$_{28}$BrN: C, 74.04; H, 6.00; N, 2.98. Found: C, 73.74; H, 5.92; N, 2.92.

EXAMPLE 2A

Alternate Preparation of N-(4-Bromophenylmethyl)-N-propylamine-N-tritylamine

A 5 liter, 3 neck, roundbottom flask affixed with thermometer, overhead stirrer, pressure-equalized addition funnel (500 ml) was charged with p-bromobenzaldehyde (185 g, 1.0 mol) followed by ethanol (978 ml). The resulting suspension was stirred for 15 minutes and then cooled to 5° C. Propylamine (131 g, 1.6 mol) was added to water (167 ml, exothermic) and added to the addition funnel. This was added to the reaction mixture over a period of 7 minutes. Upon addition of half of the propylamine solution, most of the aldehyde had dissolved and the solution became clear. The cooling bath was removed and stirring at room temperature continued for 2 hours.

Sodium borohydride (26 g, 0.69 mol) was then added in 2 gram quantities over 10 minutes. In the following 20 minutes the internal temperature had risen to 60° C. The temperature was then maintained at 55° C. for 1 hour by heating the solution on a steam bath. The reaction mixture was concentrated in vacuo (50 mm Hg/45° C.). Ethyl acetate (1.0 liter) was added with stirring, resulting in the separation of borate salts which were filtered on a coarse-frit sintered glass funnel. The organic phase was concentrated in vacuo to yield an oil. The oil was dissolved in toluene (500 ml) and concentrated to a constant mass at 50° C. in vacuo. The resulting nearly colorless clear oil was dissolved in methylene chloride (1.0 liter) and added to a 5 liter, 3 neck, roundbottom flask affixed with a thermometer, overhead stirrer, pressure-equalized addition funnel (500 ml) and calcium sulfate drying tube and the flask was immersed in an ice bath. The addition funnel was charged with a solution of trityl chloride (287 g, 1.03 mol) and methylene chloride (800 ml). The trityl chloride solution was added at a rate to maintain the internal temperature below 23° C. Then a solution of triethylamine (207 ml, 1.5 mol) in methylene chloride (120 ml) was added over 3–5 minutes while maintaining a temperature of 23° C. The resulting suspension was stirred for 12 hours at ambient temperature. Water (700 ml) was then added. The phases were shaken and separated and the organic phase washed with 10% brine (700 ml) and water (700 ml). The organic phase was then concentrated in vacuo to give an orange oil. This was transferred to a 5 liter flask and isopropyl alcohol (2 liters) was added and the solution was heated with stirring to reflux for 2 hours. After cooling to ambient temperature, the resulting precipitate was filtered to give the desired product as a colorless solid. m.p. 136°–137° C.

EXAMPLE 3

N-[2'-(4,4-Dimethyl-4,5-dihydro-oxazol-2-yl)-biphenyl-4-ylmethyl]-N-propyl-N-tritylamine To a solution of the compound resulting from Example 2 (47.0 g, 0.1 mol) dissolved in anhydrous tetrahydrofuran (300 mL) at ambient temperature under nitrogen was added magnesium turnings (2.55 g, 0.105 mol). The reaction mixture was heated to reflux at which time 1,2-dibromoethane (0.43 mL) was added to initiate Grignard formation. After refluxing for 6 hours, most of the magnesium had been consumed. The reaction mixture was then allowed to cool to ambient temperature and 1-methoxy-2-(4,4-dimethyl-4,5-dihydro-oxazol-2-yl)benzene (21.54 g, 0.105 mol) was added in one portion. The reaction mixture was allowed to stir at ambient temperature overnight and then quenched by the addition of saturated aqueous ammonium chloride (300 mL) and diluted with ethyl acetate (700 mL). The organic layer was separated, washed with 5% sodium hydrogen sulfate, water, 5% aqueous sodium bicarbonte and brine, dried over magnesium sulfate and concentrated under a reduced pressure to give a yellow oil. The crude product was crystallized from methanol (200 mL) to give 44.5 g (79%) of the title compound. m.p. 151°–153° C. $^1$H NMR (CDCl$_3$, 300 MHz) δ0.48 (t, J=7.5 Hz, 3H), 0.94–1.08 (m, 2H), 1.32 (s, 6H), 2.27 (m, 2H), 3.64 (bs, 2H), 3.79 (s, 2H), 7.18 (dd, J$_1$=J$_2$=7.2 Hz, 3H), 7.29 (dd, J=7.2 Hz, 7.5 Hz, 6H), 7.33–7.45 (m, 4H), 7.48 (ddd, J=7.5 Hz, 7.5 Hz, 1.5 Hz, 1H), 7.56 (d, J=7.5 Hz, 2H), 7.65 (d, J=7.5 Hz, 6H), 7.74 (d, J=7.2 Hz, 1H). IR (KBr) 2960, 1652, 1017, 710 cm$^{-1}$. MS (DCl/NH$_3$) m/e 564 (M+H)$^+$. Anal calcd for $C_{40}H_{40}N_2O$: C, 85.06; H, 7.14; N, 4.96. Found: C, 85.41; H, 7.09; N, 4.84.

EXAMPLE 4

N-[2'-(4,4-Dimethyl-4,5-dihydro-oxazol-2-yl)-biphenyl-4-ylmethyl]-N-propylamine

The compound resulting from Example 3 (21.0 g, 37.0 mmol) dissolved in methanol (16 mL), water (16 mL) and acetic acid (16 mL) was stirred at reflux for 2 hours. The reaction mixture was allowed to cool to ambient temperature and then the methanol was removed under reduced pressure. Ethyl acetate (500 mL) and 1N hydrochloric acid (50 mL) were added. The aqueous layer was separated and the organic layer extracted with 1N hydrochloric acid (10 mL). The combined aqueous extracts were washed with ethyl acetate (100 mL), basified with 2N sodium hydroxide (~45 mL) and extracted with ethyl acetate (3×200 mL). The combined organic extracts were washed with brine, dried over magnesium sulfate and concentrated under reduced pressure to give the title compound (9.42 g, 79%) as a viscous oil. $^1$H NMR (CDCl$_3$, 300 MHz) δ0.94 (t, J=7.5 Hz, 3H), 1.30 (s, 6H), 1.56 (m, 3H), 2.63 (t, J=7.5 Hz, 2H), 3.80 (s, 2H), 3.84 (s, 2H), 7.31-7.42 (bm, 6H), 7.47 (m, 1H), 7.72 (bd, J=7.8 Hz, 1H). IR (film) 2960, 1655, 1180 cm$^{-1}$. MS (DCl/NH$_3$) m/e 323 (M+H)$^+$.

EXAMPLE 4A

Alternate Preparation of N-[2'-(4,4-Dimethyl-4,5-dihydro-oxazol-2-yl)-biphenyl-4-ylmethyl]-N-propylamine To a 1 liter Erlenmeyer flask equipped with a mechanical overhead stirrer and charged with the resulting product of Example 3 (100 g, 0.177 mol) was added methanol (300 ml), followed by glacial acetic acid (100 ml) followed by water (100 ml). The resulting suspension was stirred vigorously at 23° C. for 24 hours. To the resulting suspension was added water (250 ml) and stirring was continued for 20 minutes. The suspension was suction filtered and the filter cake was washed with water (2×25 ml). The aqueous washes and mother liquor were combined and aqueous sodium hydroxide (24% w/w, 7.6M) was added over a period of 10 minutes until a pH of 10 was achieved (about 220 ml added). The resulting cloudy solution was concentrated to half of its original volumn in vacuo (50° C. bath/at about 100 mm Hg) over a period of 1 hour. The resulting aqueous solution was extracted with toluene (2×250 ml). The combined organic extract was washed with water (2×250 ml) and concentrated in vacuo to give the desired product as a dark yellow viscous oil.

EXAMPLE 5

Methyl 2-{N-Propyl-N-[(2'-[4,4-dimethyl-4,5-dihydro-oxazol-2-yl]biphenyl-4-yl)methyl]amino}pyridine-3-carboxylate The compound resulting from Example 4 (322 mg, 1 mmol), triethylamine (303 mg, 3 mmol) and methyl 2-chloronicotinate (222 mg, 1.3 mmol) were dissolved in toluene (0.5 mL) and heated at reflux for 24 hours. After cooling to 23° C., the reaction mixture was partitioned between ethyl acetate (10 mL) and saturated sodium bicarbonate (10 mL). The organic layer was dried over magnesium sulfate and concentrated in vacuo. The residue obtained was chromatographed on silica gel eluting with 1:3 ethyl acetate/hexane to give the title compound as a viscous, colorless oil (370 mg, 81%). $^1$H NMR (CDCl$_3$, 300 MHz) δ0.82 (t, 3H), 1.30 (s, 6H), 1.55-1.65 (m, 2H), 3.29 (t, 2H), 3.79 (s, 2H), 3.82 (s, 3H), 4.70 (s, 2H), 6.69 (dd, 1H), 7.35-7.40 (m, 5H), 7.45-7.52 (m, 1H), 7.75 (dd, 1H), 7.91 (dd, 1H), 8.35 (dd, 1H). MS (DCl/NH$_3$) m/e 458 (M+H)$^+$.

EXAMPLE 6

Methyl 2-{N-Propyl-N-[(2'-cyanobiphenyl-4-yl)methyl]amino}pyridine-3-carboxylate The compound resulting from Example 5 (1.40 g, 3.06 mmol) in pyridine (10 mL) was treated with phosphorous oxychloride (0.6 mL, 6.12 mmol) and then heated at 120° C. for 4 hours. After cooling to 10−° C., ethyl acetate (50 mL) was added, and the reaction mixture was washed with 1N sodium hydroxide solution (2×10 mL), water (10 mL) and brine (10 mL), dried over magnesium sulfate, concentrated in vacuo and chased twice with 10 mL of toluene to give a yellow oil. Chromatography on silica gel eluting with 1:3 ethyl acetate/hexane afforded the title compound as a viscous colorless oil (1.11 g, 94%). $^1$H NMR (CDCl$_3$, 300 MHz) δ0.82 (s, 3H), 1.53-1.68 (m, 2H), 3.30 (t, 2H), 3.82 (s, 3H), 4.75 (s, 2H), 6.70 (dd, 1H), 7.39-7.55 (m, 5H), 7.58-7.67 (m, 1H), 7.75 (dd, 1H), 7.91 (dd, 1H), 8.28 (dd, 1H). MS (DCl/NH$_3$) m/e 386 (M+H)$^+$.

EXAMPLE 6A

Alternate Preparation of Methyl 2-{N-Propyl-N-[(2'-cyanobiphenyl-4-yl)methyl]amino}pyridine-3-carboxylate Propyl amine (110 g, 0.3407 mol), triethyl amine (194 ml, 140.8 g, 1.39 moles) and methyl 2-chloronicotinate-HCl (84.6 g, 0.408 mol) were dissolved in toluene (380 ml) contained in a 1 liter 3 neck roundbottom flask stirred with a mechanical stirrer and equipped with nitrogen. The mixture was heated to 105° C. for 60 hours. After cooling to room temperature, ethyl acetate (500 ml) and sodium bicarbonate (5% aq., 500 ml) was added. The organic layer was separated and the aqueous layer was extracted with ethyl acetate (2×200 ml). The combined organic layers were washed with water (500 ml). The organic solution was concentrated under reduced pressure to give a dark viscous oil. This oil was dissolved in pyridine (300 ml, 3.71 mol) and the solution was placed in a 1 liter 3 neck roundbottom flask equipped with a magnetic stirrer. Then phosphorous oxychloride (68 ml, 0.73 mol) was added. The mixture was heated to 75° C. for about 3 hours. After cooling to 5° C., the mixture was carefully diluted with ethyl acetate (500 ml). Sodium hydroxide (1N in water, 120 ml) was then slowly added. The organic layer was separated. The aqueous layer was extracted with ethyl acetate (2×300 ml). The organic layers were combined and washed with sodium hydroxide (1N in water, 2×50 ml) and water (100 ml). Concentration under vacuum, followed by concentration from toluene solution (2×150 ml), gave a dark brown oil. This oil was dissolved in methanol (330 ml) and activated charcoal (5 g) was added. The mixture was heated to reflux for 15 minutes and filtered hot through Celite. The filtrate was cooled to room temperature and stirred for 24 hours. The resulting solid was filtered, washed with methanol and dried under vacuum to give the desired product as an off-white solid.

EXAMPLE 7

Methyl 2-{N-Propyl-N-[(2'-[1H-tetrazol-5-yl]biphenyl-4-yl)methyl]amino}pyridine-3-carboxylate To the compound resulting from Example 6 (29 mg, 75 μmol) in enough toluene to make a 0.50 molar solution was added trimethylsilyl azide (15 μL, 110 μmol) and dibutyltin oxide (2.0 mg, 8 μmol). The reaction mixture was heated at ~105° C. for 2.25 hours. Additional trimethylsilylazide (30 μL) was added and heating was continued. After 18 hours, additional trimethylsilylazide (30 μL) was added. After 7.25 hours, an additional aliquot (30 μL) was added. After a total of 94 hours, the reaction mixture was cooled to ambient temperature, concentrated under reduced pressure and flash chromatographed on silica gel eluting with methanol in methylene chloride to afford the title compound (11.1 mg). $^1$H NMR (CDCl$_3$, 300 MHz) δ0.83 (t, J=7 Hz, 3H), 1.63 (tq, J=7 Hz, 7 Hz, 2H), 3.29 (t, J=7 Hz, 2H), 3.84 (s, 3H), 4.62 (s, 2H), 6.69 (dd, J=5 Hz, 7 Hz, 1H), 7.12 (d, J=9 Hz, 2H), 7.25 (d, J=9 Hz, 2H), 7.43 (dd, J=2 Hz, 7 Hz, 1H), 7.5–7.65 (m, 2H), 7.91 (dd, J=2 Hz, 8 Hz, 1H), 8.09 (dd, J=2 Hz, 4.5 Hz, 1H), 8.19 (dd, J=1 Hz, 8 Hz, 1H). MS (DCl/NH$_3$) m/e 429 (M+H)+.

EXAMPLE 8

4-Methyl-2'-[1H-tetrazol-5-yl]biphenyl

To 4-methyl-2'-cyanobiphenyl (53 mg, 0.274 mmol) dissolved in toluene (0.5 mL) was added trimethylsilyl azide (100 μL, 0.73 mmol) and dibutyltin oxide (74 mg, 0.300 mmol). The reaction mixture was heated at ~105° C. for 91 hours, cooled to ambient temperature, concentrated under reduced pressure and flash chromatographed on silica gel eluting with methanol in methylene chloride to give the title compound (61.2 mg). The 300 MHz $^1$H NMR spectrum was found to be consistent with the desired product.

EXAMPLE 9

5-(2-Aminophenyl)tetrazole

To 2-cyanoaniline (5.00 g, 42.3 mmol) and dibutyltin oxide (520 mg, 2.1 mmol) dissolved in toluene (40 mL) was added trimethylsilyl azide (6.40 mL, 47 mmol). The reaction mixture was heated at ~95° C. for 70 hours, cooled to ambient temperature, concentrated under reduced pressure and partitioned between water (50 mL) and saturated sodium carbonate solution (50 mL). The organic phase was extracted with another aliquot (25 mL) of saturated sodium carbonate solution. The combined aqueous extracts were washed with ether (2×25 mL), acidified with solid citric acid to pH 4–5, and extracted with ethyl acetate (2×100 mL). The combined organic extracts were washed with brine, dried over magnesium sulfate, decolorized with Norite, filtered and concentrated under reduced pressure to give the title compound as a solid (1.20 g). $^1$H NMR (DMSO-d$_6$, 300 MHz) δ3.4 (br s, 1H), 6.68 (dt, J=1 Hz, 8 Hz, 1H), 6.90 (d, J=8 Hz, 1H), 7.25 (d,t J=1 Hz, 8 Hz, 1H), 7.73 (d, J=8 Hz, 1H), 9.0–11.0 (br, 2H). MS (DCl/NH$_3$) m/e 162 (M+H)+, 179 (M+H+NH$_3$)+.

EXAMPLE 10

5-(3-Methoxycarbonylphenyl)tetrazole

A mixture of methyl 3-cyanobenzoate (320 mg, 1.98 mmol), dibutyltin oxide (49.7 mg, 0.20 mmol) and trimethylsilyl azide (0.54 mL, 3.96 mmol) in toluene (4.0 mL) was heated at reflux for 24 hours. The solvent was removed under reduced pressure and chased with methanol (1–2 mL). The residue obtained was flash chromatographed on silica gel eluting with acetic acid and methanol in methylene chloride to give the title compound (395.7 mg). $^1$H NMR (DMSO-d$_6$, 300 MHz) δ3.0–4.5 (br, 1H), 3.92 (s, 3H), 7.75 (t, J=8 Hz, 1H), 8.11 (d, J=8 Hz, 1H), 8.32 (d, J=8 Hz, 1H), 8.54 (s, 1H). MS (DCl/NH$_3$) m/e 205 (M+H)+, 222 (M+H+NH$_3$)+.

EXAMPLE 11

5-(3-Methoxycarbonylmethylphenyl)tetrazole

A mixture of methyl 3-cyanophenyl acetate (202 mg, 1.15 mmol), dibutyltin oxide (29.0 mg, 0.116 mmol) and trimethylsilyl azide (0.31 mL, 2.28 mmol) in toluene (2.3 mL) was heated at reflux for 24 hours. The solvent was removed under reduced pressure and chased with methanol (1–2 mL). The residue obtained was flash chromatographed on silica gel eluting with acetic acid and methanol in methylene chloride to give the title compound (157.6 mg). $^1$H NMR (DMSO-d$_6$, 300 MHz) δ3.65 (s, 3H), 3.82 (s, 2H), 4.0–7.0 (br, 1H), 7.45 (d, J=8 Hz, 1H), 7.54 (t, J=8 Hz, 1H), 7.93 (d, J=8 Hz, 1H), 7.97 (s, 1H). MS (DCl/NH$_3$) m/e 219 (M+H)+, 236 (M+H+NH$_3$)+.

EXAMPLE 12

5-(2-Bromophenyl)tetrazole

A mixture of 2-cyanophenyl bromide (1.00 g, 5.49 mmol), dibutyltin oxide (90.4 mg, 0.549 mmol) and trimethylsilyl azide (1.26 g, 10.98 mmol) in toluene (10.9 mL) were heated at 93° C. for 72 hours. The solvent was removed under reduced pressure and chased with methanol. The residue obtained was partitioned between ethyl acetate (25 mL) and 10% sodium bicarbonate solution (25 mL). The organic phase was extracted with an additional aliquot of 10% sodium bicarbonate solution. The combined aqueous extracts were acidified to pH 2 with 10% hydrochloric acid and extracted with ethyl acetate (2×25 mL). The combined organic extracts were dried over magnesium sulfate, filtered, and concentrated in vacuo to give the title compound (190 mg. 74%) as a white solid. $^1$H NMR (CD$_3$OD, 300 MHz) δ7.48–7.6 (m, 2H), 7.70 (dd, J=2 Hz, 7 Hz, 1H), 7.84 (dd, J=1 Hz, 6 Hz, 1H). HRMS (DCl/NH$_3$) m/e, calcd for C$_7$H$_6$N$_4$$^{79}$Br: 224.9776, found 224.9762. IR (KBr) 3440, 2600, 1602, 1056, 748 cm$^{-1}$. Anal calc for C$_7$H$_6$N$_4$Br: C, 37.36; H, 2.24; N, 24.90. Found: C, 37.44; H, 2.25; N, 24.77.

EXAMPLE 13

5-(3-Bromophenyl)tetrazole

The title compound was prepared by the procedure described in Example 12 starting with 3-cyanophenyl bromide (1.00 g, 5.49 mmol) to give 990 mg (80%) of the title compound as a white solid. $^1$H NMR (CD$_3$OD, 300 MHz) δ7.50 (t, J=8 Hz, 1H), 7.75 (ddd, J=1 Hz, 2 Hz, 8 Hz, 1H), 8.02 (dt, J=8 Hz, 1 Hz, 1H), 8.23 (t, J=1 Hz, 1H). HRMS (DCl/NH$_3$) m/e, calc. for C$_7$H$_6$N$_4$$^{79}$Br: 224.9776, found 224.9765. IR (KBr) 3450, 3020, 2900, 2760, 1570, 1470, 742 cm$^{-1}$. Anal calcd for C$_7$H$_6$N$_4$Br: C, 37.36; H, 2.24; N, 24.90. Found: C, 36.13,; H, 2.11; N, 24.09.

EXAMPLE 14

5-(1-Naphthyl)tetrazole

The title compound was prepared by the procedure described in Example 12 starting with 1-naphthonitrile (1.00 g, 6.53 mmol) to give 1.01 g (79%) of the title compound as a white solid. $^1$H NMR (CD$_3$OD, 300 MHz) δ7.6–7.7 (m, 3H), 7.88 (dd, J=1 Hz, 7 Hz, 1H), 8.02 (dd, J=3 Hz, 4 Hz, 1H), 8.06 (dd, J=1 Hz, 12 Hz, 1H), 8.14 (d, J=8 Hz, 1H), 8.35–8.6 (m, 1H). HRMS (DCl/NH$_3$) m/e, calcd for C$_{11}$H$_8$N$_4$: 196.0749, found 196.0756. IR (KBr) 3440, 2720, 1050, 802, 770 cm$^{-1}$. Anal calcd for C$_{11}$H$_8$N$_4$: C, 67.34; H, 4.11; N, 28.56. Found: C, 66.85; H, 4.09; N, 27.54.

EXAMPLE 15

5-Phenyltetrazole

The title compound was prepared by the procedure described in Example 12 starting with benzonitrile (1.00 g, 9.69 mmol) to give 850 mg (60%) of the title compound as a white solid. $^1$H NMR (CD$_3$OD, 300 MHz) δ7.55–7.65 (m, 3H), 8.0–8.1 (m, 2H). HRMS (DCl/NH$_3$) m/e, calcd for C$_7$H$_7$N$_4$: 147.0671, found 147.0688. IR (KBr) 3440, 2700, 2610, 1605, 1561, 728 cm$^{-1}$. Anal calcd for C$_7$H$_6$N$_4$: C, 57.52; H, 4.14; N, 38.34. Found: C, 57.27; H, 3.99; N, 38.25.

EXAMPLE 16

Alternate Preparation of Methyl 2-{N-Propyl-N-[(2'-[1H-tetrazol-5-yl]biphenyl-4-yl)methyl]amino}pyridine-3-carboxylate Trimethylsilyl azide (23 g, 0.2 mol) was added to a solution of the compound resulting from Example 6 (38.5 g, 0.1 mol) in toluene (500 mL) under nitrogen. Dimethyltin oxide (1.64 g, 0.01 mol) was added and the resulting suspension heated at 100° C. for 48 hours. The mixture was cooled to ambient temperature and washed successively with water, 5% aqueous hydrochloric acid and water. The first water wash was back-extracted with methylene chloride. The combined organic extracts were dried and concentrated under reduced pressure. The residue obtained was recrystallized from ethyl acetate to give the title compound (30.3 g, 71%). m.p. 146°–147° C. $^1$H NMR (DMSO-d$_6$, 300 MHz) δ0.73 (t, 3H), 1.42–1.55 (m, 2H), 3.19 (t, 2H), 3.82 (s, 3H), 4.69 (s, 2H), 6.76 (dd, 1H), 7.01 (d, 2H), 7.21 (d, 2H), 7.51–7.60 (m, 2H), 7.61–7.69 (m, 2H), 7.83 (dd, 1H), 8.22 (dd, 1H). MS (DCl/NH$_3$) m/e 429 (M+H)$^+$.

EXAMPLE 17

N-Propyl-N-[(2'-[1H-tetrazol-5-yl]biphenyl-4-yl)methyl]amine

EXAMPLE 17A

N-Propyl-N-[(2'-Cyanobiphenyl-4-yl)methyl]amino

A mixture of the compound resulting from Example 4 (0.95 g, 2.95 mmol) in anhydrous pyridine (12 mL) was treated with phosphorus oxychloride (0.83 mL, 8.85 mmol, 3 equivalents) and then heated to reflux under nitrogen. The reaction mixture was stirred at reflux for 4 hours and then allowed to cool to ambient temperature. The pyridine was removed under reduced pressure to give a dark oil which was dissolved in 12 mL of ethanol and treated with 6N sodium hydroxide (5.9 mL, 35.4 mmol) at 0° C. The reaction mixture was allowed to stir at 0° C. for 2 hours and then poured into a separatory funnel containing 100 mL of ethyl acetate. The organic layer was separated, washed with water and brine, dried over magnesium sulfate, filtered, and concentrated under reduced pressure to give the title compound as a brown oil (390 mg, 53%). $^1$H NMR (CDCl$_3$, 300 MHz) δ0.95 (t, J=7.5 Hz, 3H), 1.58 (m, 2H), 2.65 (t, J=7 Hz, 2H), 3.87 (s, 2H), 7.40–7.56 (overlapping m, 6H), 7.63 (ddd, J=7.5 Hz, 7.5 Hz, 1.5 Hz, 1H), 7.76 (dd, J=4 Hz, 1.5 Hz, 1H). MS (DCl/NH$_3$) m/e 251 (M+H)$^+$, 268 (M+H+NH$_3$)$^+$. IR (CHCl$_3$) 2225, 1597, and 1478 cm$^{-1}$.

EXAMPLE 17B

N-Propyl-N-[(2'-[1H-tetrazol-5-yl]biphenyl-4-yl)methyl]amine

To a stirred solution of the compound resulting from Example 17A (250 mg, 1.0 mmol) in anhydrous toluene was added trimethylsilylazide (292 μL, 2.2 mmol) and dimethyltin oxide (32 mg, 0.2 mmol). The mixture was heated to reflux under nitrogen. After 30 hours under reflux, the mixture was cooled to ambient temperature and the solvent removed under reduced pressure. The resultant oil was dissolved in methanol (5 mL) and concentrated under reduced pressure to an oil; this procedure was repeated three times. The resultant oil was then dissolved in ethyl acetate and acidified with 1N hydrogen chloride in ether. The resultant solid was filtered, washed with ether and dried to give 260 mg (79%) of the title compound as its hydrochloride salt. $^1$H NMR (CD$_3$OD, 300 MHz) δ0.98 (t, J=7.5 Hz, 3H), 1.67 (m, 2H), 2.95 (m, 2H), 3.64 (s, 2H), 7.17 (bd, J=8 Hz, 2H), 7.28 (bd, J=8 Hz, 2H), 7.40–7.58 (m, 4H). MS (DCl/NH$_3$) m/e 294 (M-HCl+H)$^+$, 322 (M-HCl+H+NH$_3$)$^+$.

EXAMPLE 18

Alternate Preparation of Methyl 2-{N-Propyl-N-[(2'-[1H-tetrazol-5-yl]biphenyl-4-yl)methyl]amino}pyridine-3-carboxylate Trimethylsilyl azide (15 g, 17.5 mL, 130 mmol) was added to a solution of the compound resulting from Example 6 (25 g, 65 mmol) in toluene (125 mL). Dibutytin oxide (17 g, 65 mmol) was then added and the mixture heated at 85° C. for 20–24 hours. The reaction was cooled to ambient temperature and acetonitrile (5 mL) was added. The mixture was then heated to 82° C. for 18–22 hours. IR analysis showed complete disappearance of the azide absorption. The mixture was then cooled to 25° C. and diluted with methylene chloride (375 mL). The solution was washed three times with 1N hydrochloric acid (3×250 mL) and three times with water (3×250 mL). The solvent was removed under reduced pressure and the resulting oil was dissolved in hot toluene (125 mL) and cooled to ambient temperature. The solid was filtered and dried at 25° C. under vacuum and then recystallized by dissolving in hot ethyl acetate (200 mL) and cooling to 5° C. The resulting solid was filtered and dried at 50° C. under vacuum to afford 16.6 g (60%) of the title compound.

EXAMPLE 19

5-n-Pentyltetrazole

A mixture of hexanenitrile (938 mg, 9.65 mmol), dibutyltin oxide (293 mg, 0.98 mmol) and 97% trimethylsilylazide (2.60 mL, 19.1 mmol) in toluene (20 mL) were heated at ~110° C. for 25 hours and ambient temperature for one hour. The reaction mixture was extracted with 1M sodium hydroxide solution (4×10 mL) and the combined aqueous extracts were acidified with 6M hydrochloric acid to pH 3–4 and extracted with 10% isopropanol in chloroform (3×10 mL). The combined organic extracts were washed with brine, dried over magnesium sulfate and concentrated in vacuo to afford 950 mg (70%) of the title compound. $^1$H NMR (CDCl$_3$, 300 MHz) δ0.87 (t, J=7 Hz, 3H), 1.30–1.45 (m, 4H), 1.90 (pentet, J=7 Hz, 2H), 3.12 (t, J=7 Hz, 2H). $^{13}$C NMR (CDCl$_3$, 75 MHz) 13.70, 22.06, 23.35, 27.31, 31.05, 156.97. IR (CDCl$_3$) 2900, 1555 cm$^{-1}$. MS (DCl/NH$_3$) m/e 141 (M+H)$^+$, 158 (M+H+NH$_3$)$^+$. Anal calcd for C$_6$H$_{12}$N$_4$: C, 51.41; H, 8.63; N, 39.97. Found: C, 51.25; H, 8.59; N, 39.93.

EXAMPLE 20

5-n-Butyltetrazole

Following the procedure described in Example 21, valeronitrile (845 mg, 10.16 mmol) was reacted with dibutyltin oxide (254 mg, 1.02 mmol) and trimethylsilyl azide (2.70 ml, 19.8 mmol) in toluene (20 mL) to give 1.088 g (85%) of the title compound. $^1$H NMR (CDCl$_3$, 300 MHz) δ0.95 (t, J=7 Hz, 3H), 1.43 (sextet, J=7 Hz, 2H), 1.87 (pentet, J=7 Hz, 2H), 3.12 (t, J=7 Hz, 2H). $^{13}$C NMR (CDCl$_3$, 75 MHz) 13.42, 22.04, 23.08, 29.62, 156.94. IR (CDCl$_3$) 2900, 1555 cm$^{-1}$. MS (DCl/NH$_3$) m/e 127 (M+H)$^+$, 144 (M+H+NH$_3$)$^+$. Anal calcd for C$_5$H$_{10}$N$_4$: C, 47.60; H, 7.99; N, 44.41. Found: C, 47.14; H, 7.99; N, 43.75.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of a 5-aryltetrazole or a salt thereof of the formula:

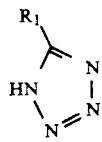

wherein R$_1$ is selected from phenyl, naphthyl,

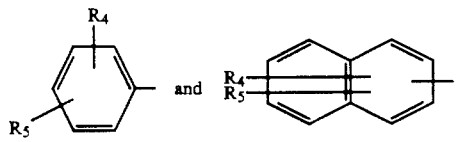

wherein R$_4$ is (1) loweralkyl, (2) halo, (3) alkoxy, (4) amino, (5) alkylamino, (6) dialkylamino, (7) alkoxycarbonyl, (8) alkoxycarbonylalkyl or

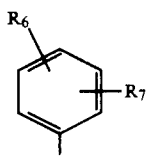

(9)

wherein R$_6$ is (i) loweralkyl, (ii) —CHO, (iii) —CO$_2$R$_8$ wherein R$_8$ is loweralkyl or a carboxy protecting group or (iv) loweralkyl substituted with —N(R$_9$)(R$_{10}$) wherein R$_9$ is hydrogen, loweralkyl, alkoxyalkyl, alkenyl, alkynyl, cycloalkyl or cycloalkylalkyl and R$_{10}$ is hydrogen, an nitrogen-protecting group or

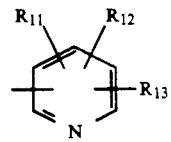

wherein R$_{11}$ is —CO$_2$R$_{14}$ wherein R$_{14}$ is loweralkyl or a carboxy protecting group and R$_{12}$ and R$_{13}$ are independently selected from hydrogen, loweralkyl and halo and R$_7$ is hydrogen, loweralkyl, alkoxy, alkoxyalkyl or halo and R$_5$ is (1) hydrogen, (2) loweralkyl, (3) alkoxy or (4) halo comprising reacting R$_1$-CN wherein R$_1$ is defined as above with (a) (R$_2$)$_3$SiN$_3$ wherein R$_2$ at each occurrence is independently selected from loweralkyl and phenyl and (b) (R$_3$)$_2$SnO wherein R$_3$ is independently selected at each occurrence from loweralkyl and phenyl or (R$_3$)$_2$ represents —(CH$_2$)$_n$— wherein n is 4, 5 or 6.

2. The process of claim 1 wherein R$_2$ is methyl and R$_3$ is methyl or butyl.

3. A process for the preparation of a compound of formula:

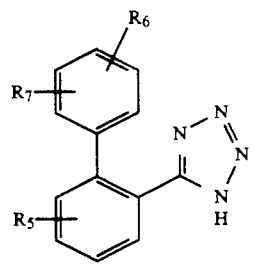

or a salt thereof wherein R$_6$ is (i) loweralkyl, (ii) —CHO, (iii) —CO$_2$R$_8$ wherein R$_8$ is loweralkyl or a carboxy protecting group or (iv) loweralkyl substituted with —N(R$_9$)(R$_{10}$) wherein R$_9$ is hydrogen, loweralkyl, alkoxyalkyl, alkenyl, alkynyl, cycloalkyl or cycloalkylalkyl and R$_{10}$ is hydrogen, an nitrogen-protecting group or

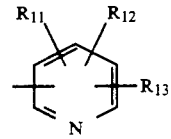

wherein

R$_{11}$ is —CO$_2$R$_{14}$ wherein R$_{14}$ is loweralkyl or a carboxy protecting group and R$_{12}$ and R$_{13}$ are independently selected from hydrogen, loweralkyl and halo;

R$_5$ is (1) hydrogen, (2) loweralkyl, (3) alkoxy or (4) halo; and

R$_7$ is (1) hydrogen, (2) loweralkyl, (3) alkoxy, (4) alkoxyalkyl or (5) halo comprising reacting a biphenyl nitrile of the formula:

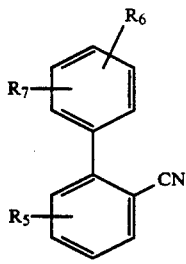

wherein $R_5$, $R_6$ and $R_7$ are defined as above with (a) $(R_2)_3SiN_3$ wherein $R_2$ at each occurrence is independently selected from loweralkyl and phenyl and (b) $(R_3)_2SnO$ wherein $R_3$ is independently selected at each occurrence from loweralkyl and phenyl or $(R_3)_2$ represents $-(CH_2)_n-$ wherein n is 4, 5 or 6.

4. The process of claim 3 wherein $R_2$ is methyl and $R_3$ is methyl or butyl.

5. The process of claim 3 wherein the proportions of reactants are one molar equivalent of biphenyl nitrile, from about 1.0 to about 8.0 molar equivalents of $(R_2)_3SiN_3$ and from about 0.05 to about 1.0 molar equivalents of $(R_3)_2SnO$.

6. A process for the preparation of a compound of formula:

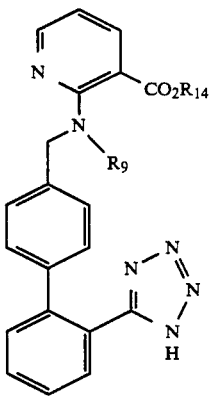

or a salt thereof wherein $R_9$ is hydrogen, loweralkyl, alkoxyalkyl, alkenyl, alkynyl, cycloalkyl or cycloalkylalkyl and $R_{14}$ is hydrogen, loweralkyl or a carboxy protecting group comprising reacting a biphenyl nitrile of the formula:

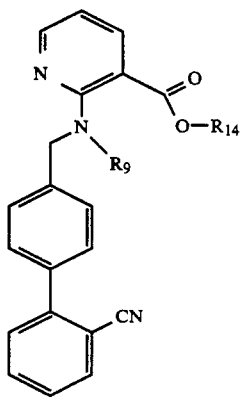

wherein $R_9$ and $R_{14}$ are as defined above with $(R_2)_3SiN_3$ wherein $R_2$ at each occurrence is independently selected from loweralkyl and phenyl and $(R_3)_2SnO$ wherein $R_3$ at each occurrence is selected from the group consisting of lower alkyl and phenyl or $(R_3)_2$ represents $-(CH_2)_n-$ wherein n is 4, 5 or 6.

7. The process of claim 6 wherein $R_2$ is methyl, $R_3$ is methyl or butyl, $R_9$ is loweralkyl and $R_{14}$ is loweralkyl.

8. The process of claim 6 wherein the proportions of reactants are one molar equivalent of biphenyl nitrile, from about 1.0 to about 8.0 molar equivalents of $(R_2)_3SiN_3$ and from about 0.05 to about 1.0 molar equivalents of $(R_3)_2SnO$.

9. A process for the preparation of a compound of formula:

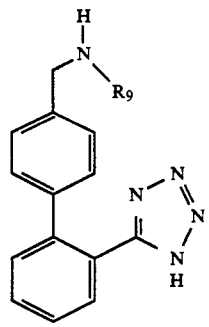

or a salt thereof wherein $R_9$ is hydrogen, loweralkyl or an nitrogen protecting group comprising reacting a biphenyl nitrile of the formula:

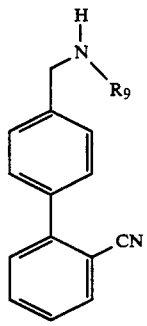

wherein $R_9$ is as defined above with with $(R_2)_3SiN_3$ wherein $R_2$ at each occurrence is independently selected from loweralkyl and phenyl and $(R_3)_2SnO$ wherein $R_3$ at each occurrence is selected from the group consisting of lower alkyl and phenyl or $(R_3)_2$ represents $-(CH_2)_n-$ wherein n is 4, 5 or 6.

10. The process of claim 9 wherein $R_2$ is methyl, $R_3$ is methyl or butyl, $R_9$ is loweralkyl.

11. The process of claim 9 wherein the proportions of reactants are one molar equivalent of biphenyl nitrile, from about 1.0 to about 8.0 molar equivalents of $(R_2)_3SiN_3$ and from about 0.05 to about 1.0 molar equivalents of $(R_3)_2SnO$.

12. A process for the preparation of a compound of formula:

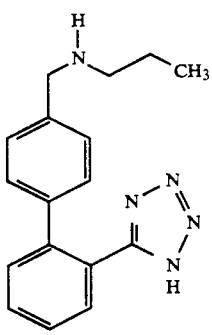

or a salt thereof comprising reacting a compound of the formula:

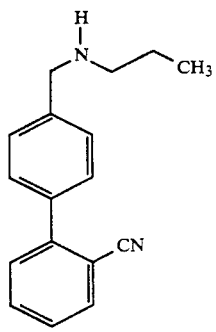

with trimethylsilyl azide and dibutyltin oxide, dimethyltin oxide or diphenyltin oxide.

13. A process for the preparation of a compound of formula:

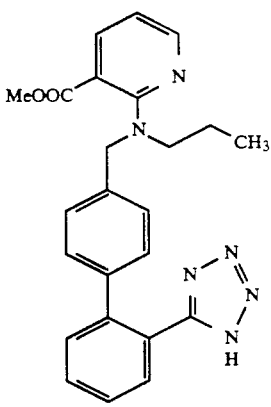

or a salt thereof comprising reacting a compound of the formula:

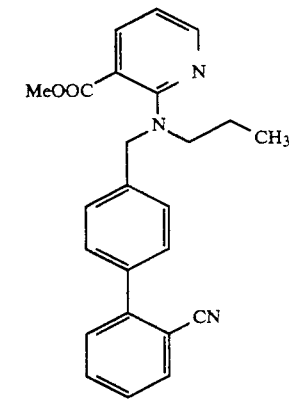

with trimethylsilyl azide and dibutyltin oxide, dimethyltin oxide or diphenyltin oxide.

* * * * *